United States Patent
Zoughi et al.

[19]

[11] Patent Number: 5,939,889
[45] Date of Patent: Aug. 17, 1999

[54] STRENGTH-RELATED TESTING OF CONCRETE USING MICROWAVE SIGNALS

[75] Inventors: Reza Zoughi; Paul S. Nowak, both of Fort Collins, Colo.

[73] Assignee: Colorado State University Research Foundation, Fort Collins, Colo.

[21] Appl. No.: 08/058,453

[22] Filed: May 7, 1993

[51] Int. Cl.⁶ .................................................. G01R 27/04
[52] U.S. Cl. ........................ 324/643; 324/647; 324/632
[58] Field of Search .................................. 324/640, 643, 324/647; 73/61.41, 54.03

[56] References Cited

U.S. PATENT DOCUMENTS

| | | | |
|---|---|---|---|
| 3,562,642 | 2/1971 | Hochschild | 324/644 |
| 4,155,035 | 5/1979 | Fitzky | 324/636 |
| 5,046,356 | 9/1991 | Osaki | 324/640 |
| 5,229,726 | 7/1993 | Kent | 324/640 |
| 5,256,978 | 10/1993 | Rose | 324/643 |

OTHER PUBLICATIONS

Rzepecka, M.A., et al., "Monitoring of Concrete Curing Process by Microwave Terminal Measurements," pp. 120–125, *IEEE Transactions on Industrial Electronics and Control Instrumentation*, vol. IECI–19, No. 4, Nov. 1974.

*Primary Examiner*—Ernest F. Karlsen
*Assistant Examiner*—Jose M. Solis
*Attorney, Agent, or Firm*—Sheridan Ross P.C.

[57] ABSTRACT

An apparatus is disclosed for testing concrete having an unknown water/cement ratio and an unknown compressive strength. The apparatus includes a transmitter assembly for transmitting microwave signals at one or more predetermined frequencies. A receiver assembly receives each microwave signal reflected from the concrete under test. The reflected microwave signals, together with the transmitted microwave signals, are used to determine a reflection coefficient magnitude for the particular microwave frequency. A processing unit uses the reflection coefficient magnitude to determine a value related to concrete strength. In one embodiment, the processing unit relies on a logarithmic function that correlates the reflection coefficient magnitude and a water/cement ratio. A value related to the compressive strength of the concrete can also be obtained using the value of the water/cement ratio or the value of the reflection coefficient magnitude.

23 Claims, 7 Drawing Sheets

5,939,889

STRENGTH-RELATED TESTING OF CONCRETE USING MICROWAVE SIGNALS

FIELD OF THE INVENTION

The present invention relates to using microwave signals for analysis of concrete and, more particularly, to automatically determining a value related to concrete strength as a function of a reflection coefficient.

BACKGROUND OF THE INVENTION

Concrete is extensively used in the construction industry. The compressive strength of concrete and its supporting capabilities are directly related to the amount of water that is utilized in proportion to the amount of cement that is mixed with the water (water/cement ratio). It would be beneficial to the building trade to be able to determine the compressive strength of concrete in a non-destructive manner, i.e., using a technique that does not cause damage to the concrete sample under inspection.

Technologies have been developed for detecting the strength of concrete and include those generally identified as: pulse velocity method, surface hardness, penetration, pull-out, break-off and maturity techniques. Some of these techniques are not completely non-destructive since some damage to the concrete results from using them. Furthermore, such techniques are limited because the accuracy and reliability of the results are not well established.

Microwave technology has also been proposed for use in analyzing concrete materials. In that regard, concrete can be characterized, like other insulating materials, as having a dielectric constant ($\epsilon$). The value of the dielectric constant for a concrete sample has been found to be a function of the water/cement (w/c) ratio. In determining the dielectric constant, a reflection coefficient (R) is determinable using the ratio of a reflected microwave from the concrete sample to the transmitted microwave that is incident upon the sample. The value of the reflection coefficient (R) is a complex quantity that includes a magnitude ($\Gamma$) and a phase ($\phi$). It has been observed that the magnitude ($\Gamma$) of the reflection coefficient varies as a function of the w/c ratio. More particularly, the magnitude of the reflection coefficient decreases as the w/c ratio increases. Since the w/c ratio is indicative of, or directly related to, the compressive strength of concrete, the reflection coefficient magnitude is useful in analyzing a concrete structure in connection with determining strength related information.

It would therefore be advantageous to provide an apparatus and method that automatically determines the water/cement ratio and/or the compressive strength of any concrete sample using microwave signals. Such microwave technology would permit non-destructive inspection or testing and would rely on the magnitude of the reflection coefficient in subsequently correlating the determined reflection coefficient magnitude with desired concrete strength related information.

SUMMARY OF THE INVENTION

In accordance with the present invention, an apparatus is disclosed for providing a value related to concrete strength, such as a value of the w/c ratio and/or concrete compressive strength. The apparatus includes a transmitter assembly for generating microwave signals at one or more predetermined frequencies for incidence upon the concrete under inspection. The transmitter assembly includes, in one embodiment, a directional coupler that receives the transmitted microwave signals at the desired frequency(ies) and directs them to a concrete sample. In the preferred embodiment, the directional coupler contacts the concrete sample. Some of the microwave energy is absorbed by the concrete sample while other microwave energy that is incident upon the concrete sample is reflected back into the directional coupler at another section thereof. This section of the directional coupler is part of a receiver assembly. The receiver assembly also includes, in one embodiment, a crystal detector in communication with the directional coupler. The crystal detector outputs a voltage signal that is related to the magnitude ($\Gamma$) of the reflection coefficient. The crystal detector communicates with a processing unit for determining desired information related to the concrete sample being tested.

In one embodiment, the processing unit, after receiving the measured data using the reflected microwave signals from the receiver assembly, determines a reflection coefficient magnitude for the frequency of the transmitted microwave signals. The determined reflection coefficient magnitude is then correlated by the processor with a value related to the strength of the concrete sample under test. In one embodiment, the processing executes a software implemented algorithm. In particular, the software implements a logarithmic function in which a value of a water/cement ratio is determined using the reflection coefficient magnitude. That is, by substituting the measured reflection coefficient magnitude into the logarithmic function, a corresponding w/c ratio is obtained. Additionally, or alternatively, a value of compressive strength is determinable using the reflection coefficient magnitude. In another embodiment, a storage memory is provided that communicates with the processing unit. The storage memory stores a number of correlated values. Specifically, a number of reflection coefficient magnitudes are stored, together with a number of values related to concrete strength, such as water/cement ratios and/or concrete compressive strength values. After the reflection coefficient magnitude is determined, it can be correlated with a specific strength related value using the information stored in the storage memory. The processing unit also communicates with a display unit for providing a display of the determined concrete strength related information (the value of the w/c ratio and/or the value of the concrete compressive strength).

Based on the foregoing, a number of worthwhile objectives of the present invention are readily seen. An apparatus is provided for automatically determining values related to concrete strength using microwave signals that are incident upon the concrete being tested. The values that are determinable include a water/cement ratio and a concrete compressive strength. Each of these two characteristics provide significant information about the quality of the concrete. In connection with the automatic determination, the apparatus correlates a reflection coefficient magnitude with a corresponding value related to concrete strength. In that regard, the apparatus relies on a previously determined relationship, such as a logarithmic function equating the reflection coefficient magnitude with a water/cement ratio or concrete compressive strength. Upon automatic determination of the concrete strength related value, it can be displayed and/or stored in memory for subsequent retrieval. The transmitter assembly is configured to separately apply a number of microwave signals at different frequencies. The adjustability of the frequency input enables the apparatus to obtain a number of reflection coefficient magnitudes that can be utilized to determine the concrete strength related value thereby providing a more accurate measurement. The apparatus is relatively simple in design and can be made portable to be hand-held by the user or operator.

Additional advantages of the present invention will become readily apparent from the following discussion, particularly when taken together with the accompanying drawings.

DETAILED DESCRIPTION

Figure 1:
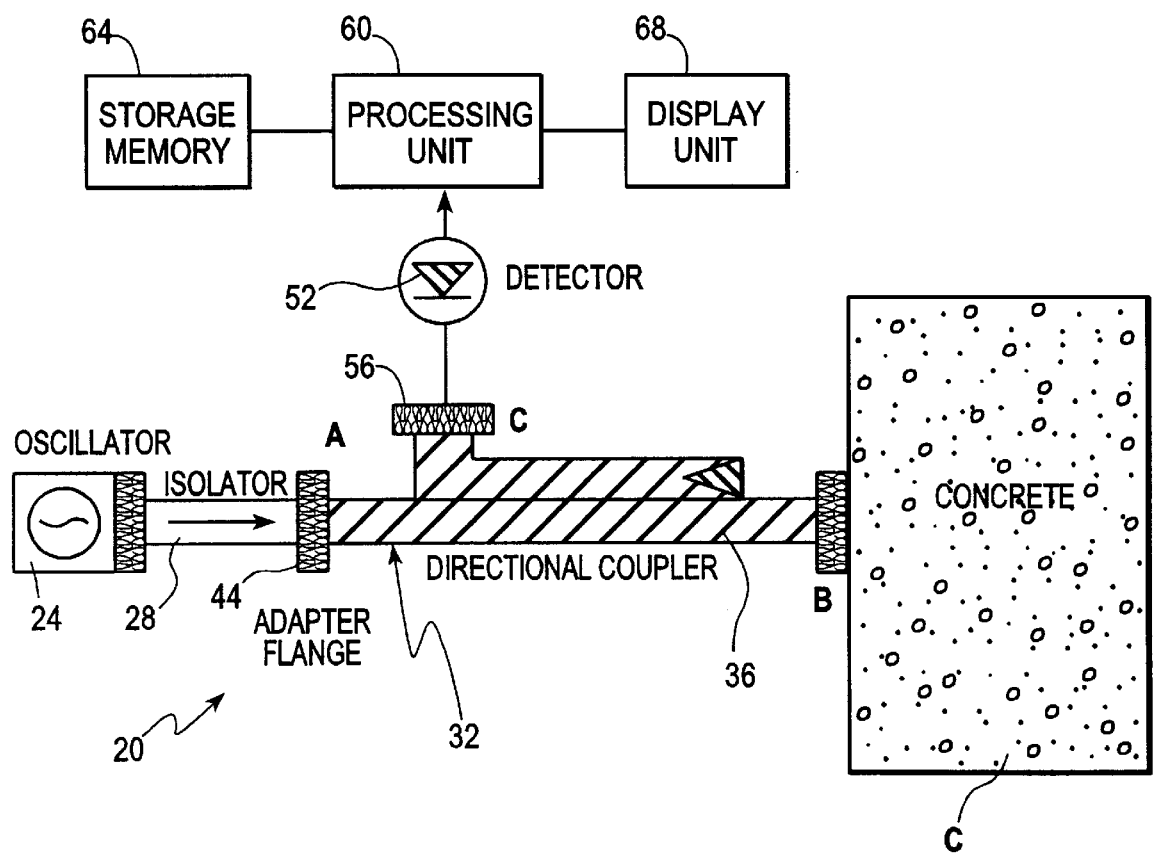
FIG. 1 is a block diagram of the present invention.

With reference to FIG. 1, one embodiment of an apparatus for analyzing concrete strength parameters is illustrated. This embodiment includes a transmitter assembly 20 for transmitting microwave signals to a concrete sample or section C that is being tested or inspected. Generally, the concrete sample is being tested to analyze its strength, with such strength being based on its compressive strength ($f_c$) and/or the water/cement (w/c) ratio of the concrete sample. Typically, concrete compressive strength decreases with increasing w/c ratios.

The transmitter assembly 20 includes an oscillator 24 for generating microwave signals at any one of a number of selected and desired microwave frequencies. The output of the oscillator 24 is inputted to an isolator 28 that receives the inputted microwave signals and isolates the signals from any unwanted signals entering the oscillator 24. The transmitter assembly 20 also includes, in this embodiment, a directional coupler 32 that receives the microwave signals from the isolator 28. The directional coupler 32 has a microwave transmitting section 36 and a microwave receiving section 40. The transmitting section 36 is connected to the isolator 28 by means of a first adapter or flange 44. The transmitting section 36 of the directional coupler 32 is preferably in contact with the concrete sample C. The transmitting section 36 directs the transmitted microwave signals relative to the concrete sample C. The transmitted microwave signals are incident upon the concrete sample C, with some of the microwave energy being absorbed by the concrete sample. Reflected microwave signals are generated due to the incidence of the transmitted microwave signals upon the concrete sample and the reflected microwave signals are received by the receiving section 40 of the directional coupler 32. The receiving section 40 is part of a receiver assembly 48 for receiving the reflected microwave signals in order to measure the signals in connection with determining the value of a reflection coefficient magnitude associated with the concrete sample C. That is, a reflection coefficient magnitude ($\Gamma$) is determined with reference to the reflection plane defined at the concrete sample C edge that is contacted by the transmitting section 36. In making the measurement, the receiving section 40 of the directional coupler 32 communicates with a crystal detector 52 of the receiver assembly 48. The receiving section 40 is connected to the crystal detector 52 by means of a second adapter or flange 56. The crystal detector 52 generates a signal as a function of the reflected and received microwave signals. This signal is applied to a processing unit 60 for use in automatically analyzing the reflected microwave signals in order to determine the desired concrete strength related parameter, such as a value of concrete compressive strength and/or a value of the water/cement ratio for the concrete sample C. This analysis and calculations will be subsequently explained in greater detail. The processing unit 60 communicates with storage memory 64 for storing program code (software) and/or data useful in correlating concrete strength related information to the measured reflected microwave signals. This correlation can be between values of reflection coefficient magnitudes and concrete strength related values (i.e., concrete compressive strengths and/or w/c ratios). This embodiment preferably also includes a display unit 68 for providing the operator or user with an immediate indication as to the value of the concrete strength related parameter for the concrete sample C.

A key aspect associated with analyzing the reflected microwave signals relates to obtaining the necessary correlation between the measured value for the reflection coefficient magnitude ($\Gamma$), based on the reflected microwave signals, and a desired concrete strength parameter. In order to describe this relationship that is necessary in order to achieve the automatic analysis and determination, reference is first made to FIG. 2. This figure shows a graph of values of reflection coefficient magnitudes as a function of curing time and w/c ratios. With regard to the value of the reflection coefficient magnitudes ($\Gamma$) of FIG. 2, they are obtained as a result of testing four cement paste blocks with dimensions of 15×15×15 $cm^3$, which were prepared with the w/c ratios of 0.31, 0.40, 0.50 and 0.60 using ASTM type II cement. The dielectric properties of each cement paste block was measured daily for 27 days, which is the time period for concrete design strength to be reached, at frequencies of 5, 9, 13 and 17 GHz. Each measurement ($\Gamma$) is an average of four measurements conducted on four sides of each cement paste block. As understood from FIG. 2, reflection coefficient magnitude values are generally different for different w/c ratios, with the values of the reflection coefficient magnitudes generally increasing with decreasing w/c ratios.

In conjunction with the analysis for determining a concrete strength parameter, the value of the reflection coefficient magnitude ($\Gamma$) is measured. This magnitude is directly related to the water/cement ratio or concrete compressive strength for the concrete sample. It has been determined that the concrete strength parameters are a function of the dielectric constant of the concrete sample. Consequently, the reflection coefficient magnitude ($\Gamma$) can be used in determining concrete strength parameters of interest. That is, the reflection coefficient magnitude ($\Gamma$) is part of a complex quantity (R), which is the ratio of the reflected microwave signals from the concrete sample to the transmitted microwave signals that are incident upon the concrete sample. The reflection coefficient (R) is a complex quantity that consists of the afore-noted reflection coefficient magnitude (Γ) and a phase (φ), namely: $R=\Gamma e^{j\phi}$. The reflection coefficient (R) is used to determine the dielectric constant of a medium, such as the concrete sample C. With respect to useful information related to the dielectric constant and its relationship to concrete strength related parameters, it is only necessary to measure and determine the reflection coefficient magnitude (Γ) and not the phase (φ). In making this determination, any one of a number of techniques can be utilized. In connection with the apparatus of FIG. 1, the value of Γ can be calculated by using the equation:

$$\Gamma = k\left[-\left[\frac{S_{CA}}{S_{BA}S_{CB}}\right] - \frac{b_c}{b_{csc}}\right] \quad (1)$$

where the values of S relate to a microwave scattering parameter that is known for the particular directional coupler 32 and the value of k relates to properties associated with the crystal detector 52. The different S values are denoted by their accompanying subscripts. The S value for $S_{CA}$, for example, is based on microwave signal related scattering relative to the output end of the receiving section 40 and the input end of the transmitting section 32, with the subscript letters being provided on FIG. 1 at the appropriate microwave transmitting/receiving location. The value of $b_c$ is the power measured at the output of the receiving section 40 for the concrete sample C. The value of $b_{scs}$ is the power measured at the output of the receiving section 40 when the concrete sample is replaced with a short circuit (SC).

Figure 2:
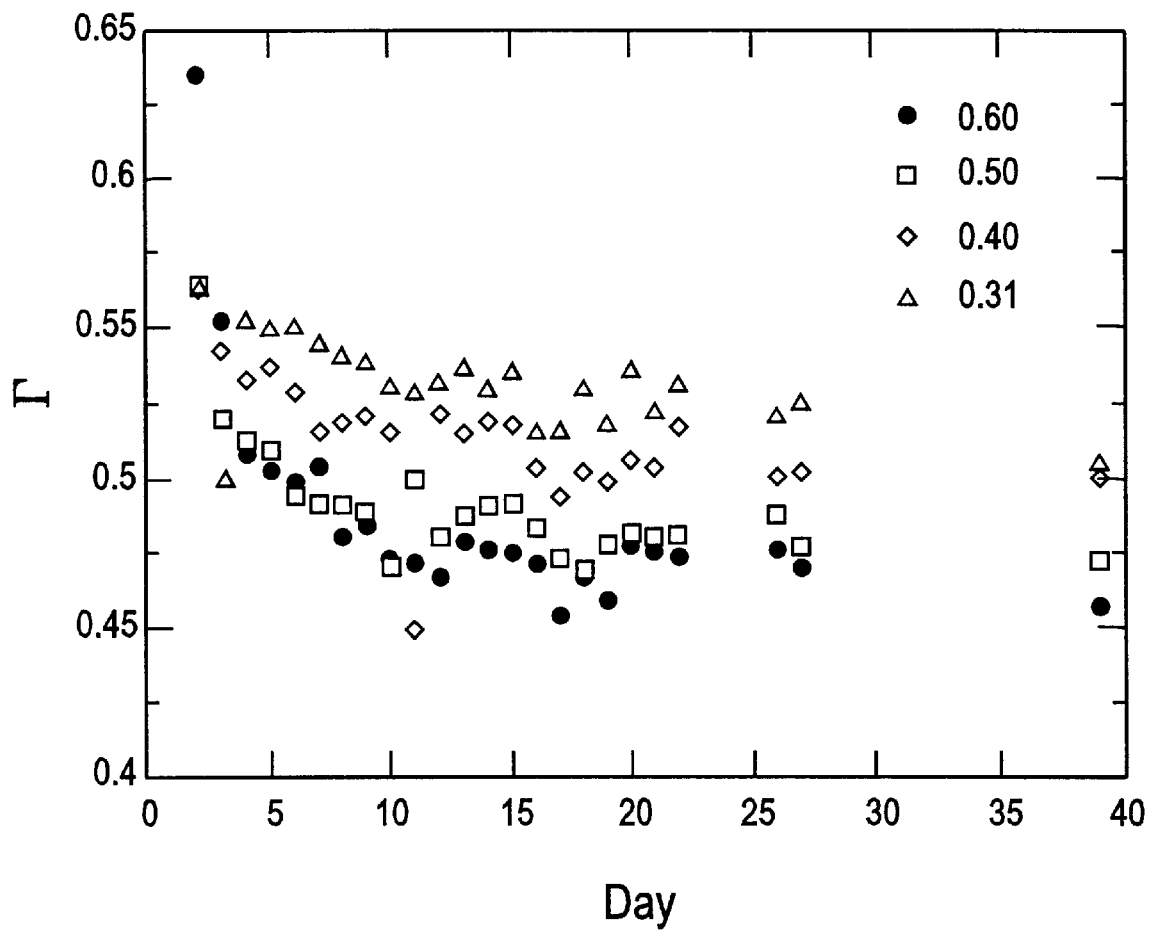
FIG. 2 is a graph illustrating the relationship between the reflection coefficient magnitude ($\Gamma$) and time (curing period), for each of a number of cement paste water/cement ratios.
Figure 3:
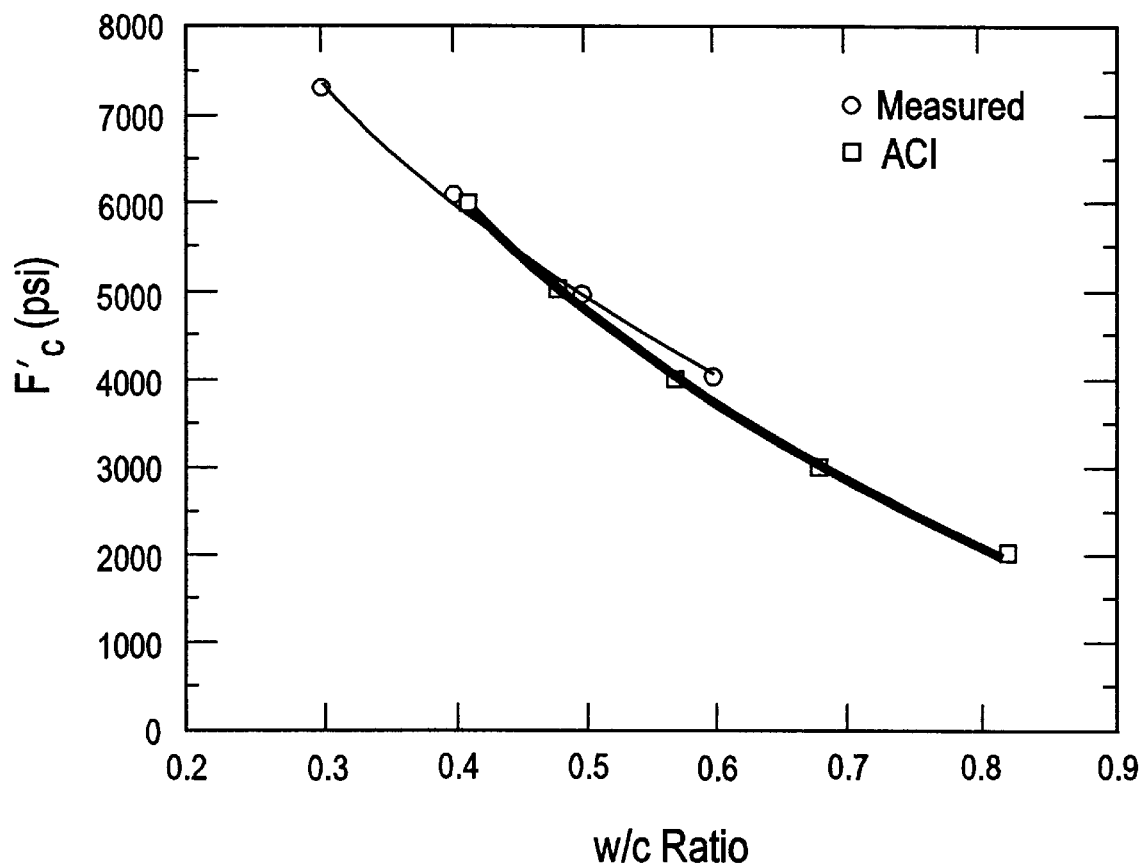
FIG. 3 is a graph illustrating the compressive strength of cement paste as a function of w/c ratios for measured values and for values obtained from a known table.

With reference to FIG. 3, additional measurements were taken of the four cured concrete samples associated with FIG. 2. The compressive strength of cured concrete is directly related to its w/c ratio. The compressive strengths of the four samples having the four different w/c ratios were measured on the fortieth day after the samples were formed using a standard strength testing machine. FIG. 3 shows the results of the strength tests, together with plotted points representative of a standard or known table (ACI) for compressive strength as a function of w/c ratios. Both sets of data, based on the measurements for the four test samples and the information from the standard table, were fitted with a logarithmic equation of the form: $f'_c=a+b\log(w/c)$. Based on this logarithmic fit, the curves of FIG. 3 were generated and each has a correlation coefficient of greater than 0.999 (the correlation coefficient is indication of how well data points fit the equation, with a correlation coefficient of one being an exact fit). The two curves correspond very closely. The standard ACI table results are based on tests of cylindrical specimens continuously moist cured. The four test samples disclosed herein were rectangular and moist cured only for three days. There is a loss of strength of about 75%–80% for specimens that are moist cured compared to those that are continuously moist cured. On the other hand, rectangular test specimens have an increase in strength of 125% when compared to the strength of cylindrical test specimens.

Based on this analysis, the concrete compressive strength for the four cement paste samples can be described as a function of the w/c ratio, namely:

$$f'_c=807.2-13261 \log(w/c) \quad (2)$$

Referring again to the four cement paste samples that were tested, the following table is provided that sets out the values of reflection coefficient magnitudes (Γ) that were obtained or measured for a particular microwave frequency and a known w/c ratio.

TABLE

Reflection Coefficient Magnitudes of Samples for Various w/c Ratios and Frequencies

| Frequency (GHz) | w/c Ratio | | | |
|---|---|---|---|---|
| | 0.31 | 0.40 | 0.50 | 0.60 |
| 5 | 0.53 | 0.49 | 0.45 | 0.40 |
| 9 | 0.52 | 0.50 | 0.48 | 0.47 |
| 13 | 0.53 | 0.51 | 0.48 | 0.48 |
| 17 | 0.51 | 0.48 | 0.47 | 0.46 |

The results from this table were used, for each microwave frequency, in calculating the percentage change (increase) in the reflection coefficient magnitude for w/c ratios of 0.50, 0.40 and 0.31 with respect to the reflection coefficient magnitude obtained for the w/c ratio of 0.60, namely:

$$\Delta\Gamma(f) = \frac{|\Gamma_{0.6}(f) - \Gamma_{w/c}(f)|}{\Gamma_{0.6}(f)} \times 100 \quad (3)$$

Figure 4:
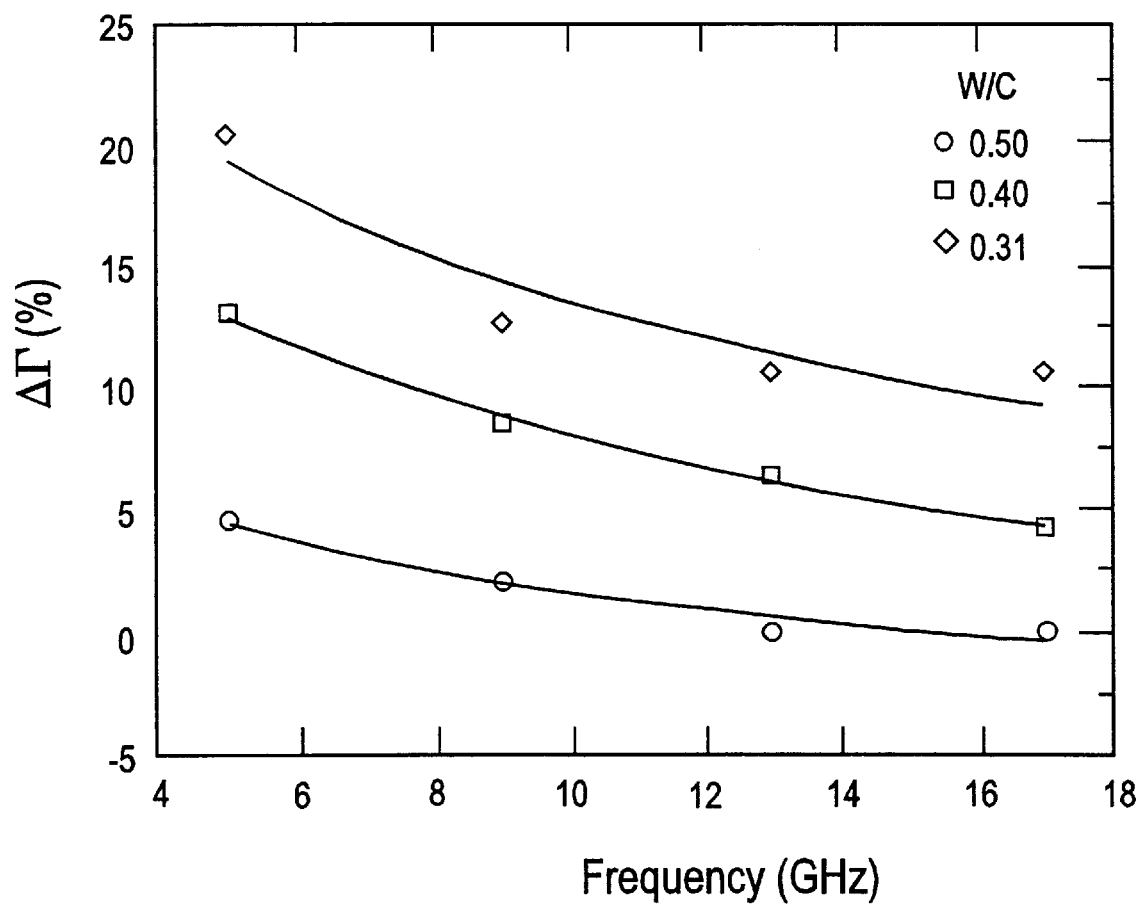
FIG. 4 is a graph illustrating the relationship between a percentage change (based on a w/c ratio of 0.6) in the reflection coefficient magnitude as a function of frequency, for each of a number of w/c ratios.

The frequency (f) is in gigahertz (GHz) and includes the following frequencies: 5 GHz, 9 GHz, 13 GHz and 17 GHz. Using the data of the table and equation (3), the points are plotted and illustrated in FIG. 4. The resulting curves through the points of FIG. 4 are generated as a logarithmic fit with the correlation coefficient >0.995 and are given by the following equations:

$$\Delta\Gamma(f)=32.78-19.16\log(f) \text{ for w/c=0.31} \quad (4)$$

$$\Delta\Gamma(f)=24.55-16.50\log(f) \text{ for w/c=0.40} \quad (5)$$

$$\Delta\Gamma(f)=10.88-0.21\log(f) \text{ for w/c=0.50} \quad (6)$$

FIG. 4 shows that, at lower frequencies, there is more separation between curves. Lower frequencies may be more sensitive for w/c ratio determinations. A swept frequency measurement of the reflection coefficient magnitude (Γ) may improve the accuracy in the determination of the w/c ratio by providing more measurement points. That is, for a concrete sample having an unknown w/c ratio, the determination of the reflection coefficient magnitude (Γ) may be based on an average of a number of measured values at different microwave frequencies that are transmitted to the concrete sample.

Figure 5:
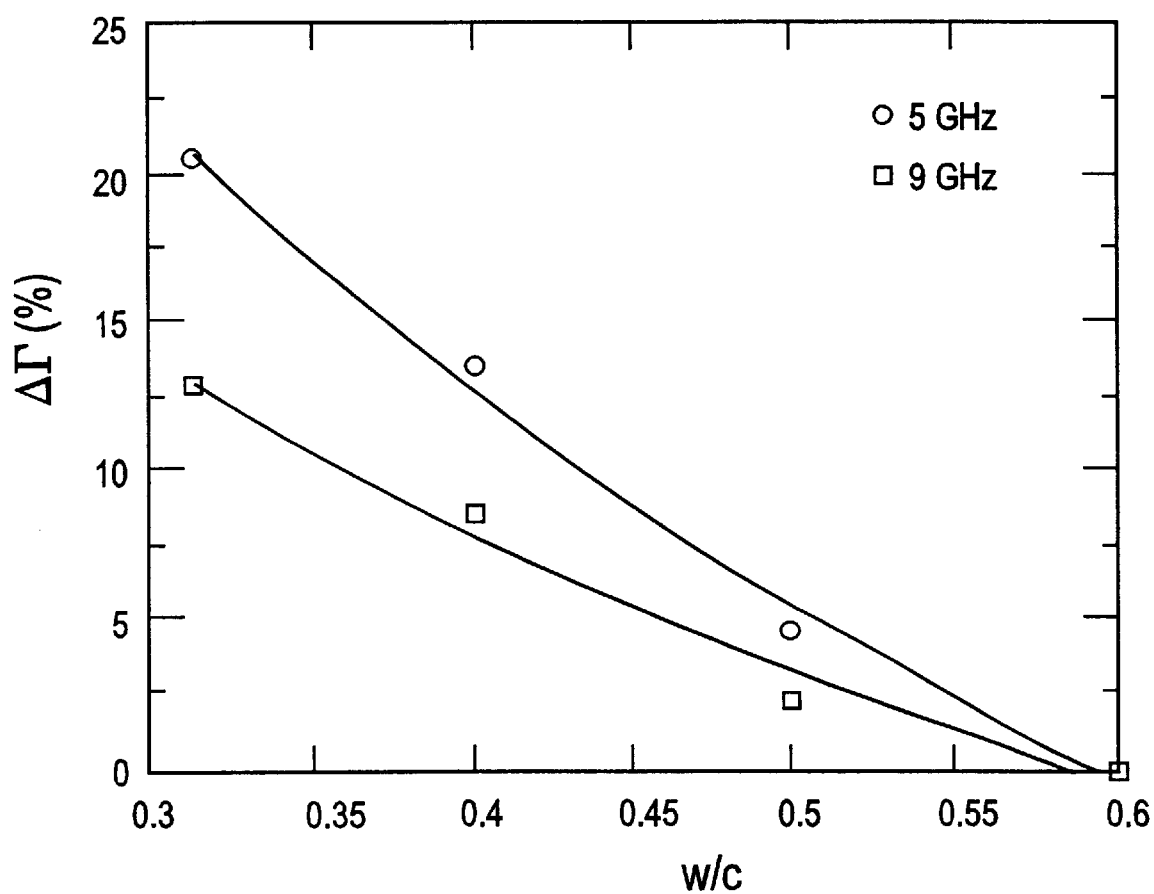
FIG. 5 is a graph illustrating the percentage change (based on a w/c ratio of 0.6) in the reflection coefficient magnitude as a function of w/c ratios for two different frequencies.

With reference to FIG. 5, the percentage change in the value of the reflection coefficient magnitude was calculated with respect to the obtained data at certain frequencies, i.e., 5 and 9 GHz. The percentage change is based on the value of the reflection coefficient magnitude for the concrete sample having a w/c ratio equal to 0.60. This percentage change in the reflection coefficient magnitude is identified as ΔΓ and the equation for determining this percentage change is:

$$\Delta\Gamma(w/c) = \frac{|\Gamma_f(0.6) - \Gamma_f(w/c)|}{\Gamma_f(0.6)} \quad (7)$$

The results obtained using equation (7) are illustrated in FIG. 5, which shows a plot of these determined points. The plotted points were numerically analyzed and it was determined that a logarithmic fit was applicable to this data. The following logarithmic equations were obtained with the correlation coefficient > than 0.995:

$$\Delta\Gamma(w/c) = -16.93 - 74.48\log(w/c) \text{ for } f=5 \text{ GHz} \qquad (8)$$

$$\Delta\Gamma(w/c) = -11.07 - 47.49\log(w/c) \text{ for } f=9 \text{ GHz} \qquad (9)$$

FIG. 5 illustrates, once again, the ability of lower microwave frequencies to better determine w/c ratios in cement paste samples. Additionally, equations (8) and (9) may be used to determine the w/c ratio for a measured $\Gamma$. The coefficients (a,b) may also be determined more precisely provided that additional data for intermediate w/c ratio values are available.

Figure 6:
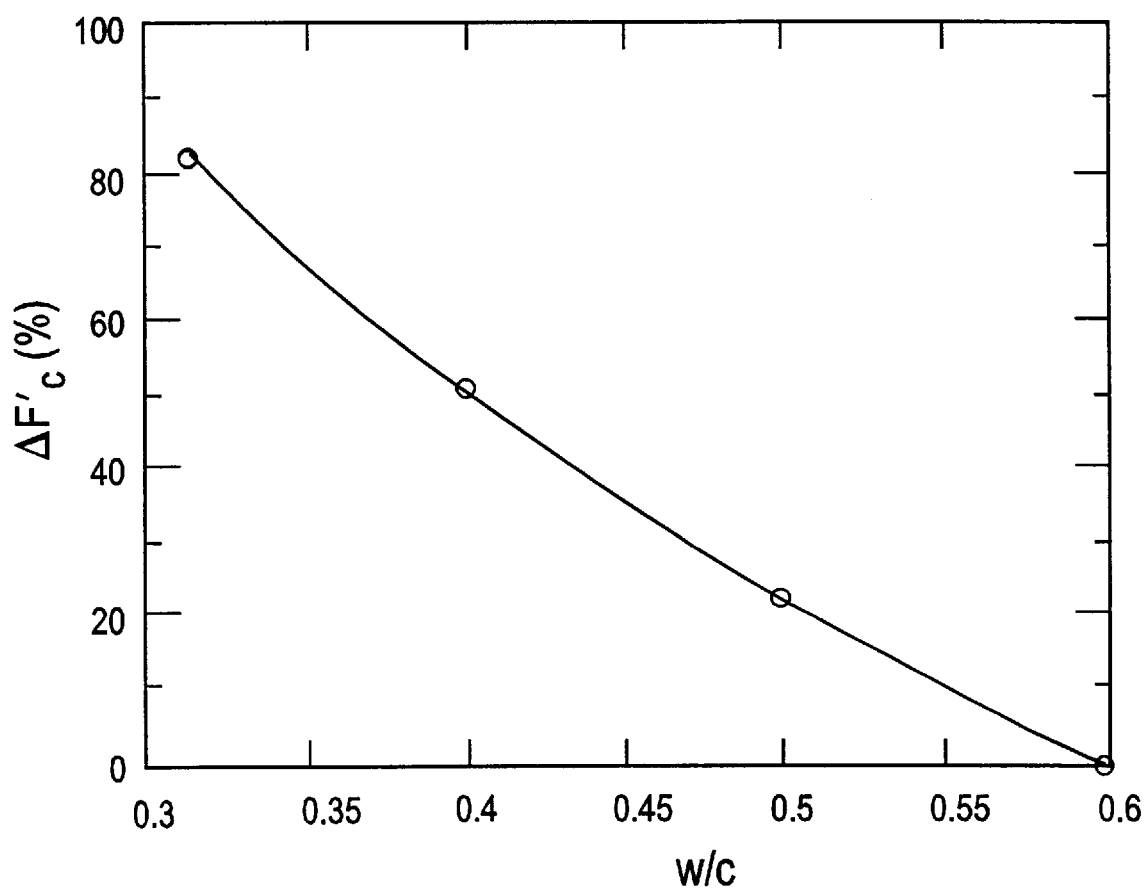
FIG. 6 is a graph illustrating the percentage change (based on a w/c ratio of 0.6) in cement paste compressive strength as a function of w/c ratios.

The percentage change in the compressive strength for each of the other three samples, with respect to the sample having the w/c ratio of 0.60, was calculated. The plotted points are illustrated in FIG. 6. The curve through the plotted points was also obtained using a logarithmic fit having a correlation coefficient >0.999. The resulting logarithmic equation for the curve of FIG. 6 is:

$$\Delta f_c = -63.97 - 289.21\log(w/c) \qquad (10)$$

The value of the compressive strength ($f'_c$) is in psi (6.89 $kN/m^2 = lb/in^2$).

In analyzing the coefficients (a,b) of equation (10), it is noted that, if lower microwave frequencies are used in equation (7), more closely matching coefficients may be achieved. This possibility is substantiated when the ratios of the coefficients for the logarithmic fit constants (b/a) are analyzed with respect to equations (8) and (9). These ratios are 4.4 and 4.3 at microwave frequencies 5 and 9 GHz, respectively. Equation (10) has a b/a ratio of 4.5, which could be matched more closely at frequencies lower than 5 GHz. This is further supported by the premise that microwaves generally penetrate deeper into dielectric materials at lower frequencies, which may result in a sensing of more of the concrete sample (cement paste).

Figure 7:
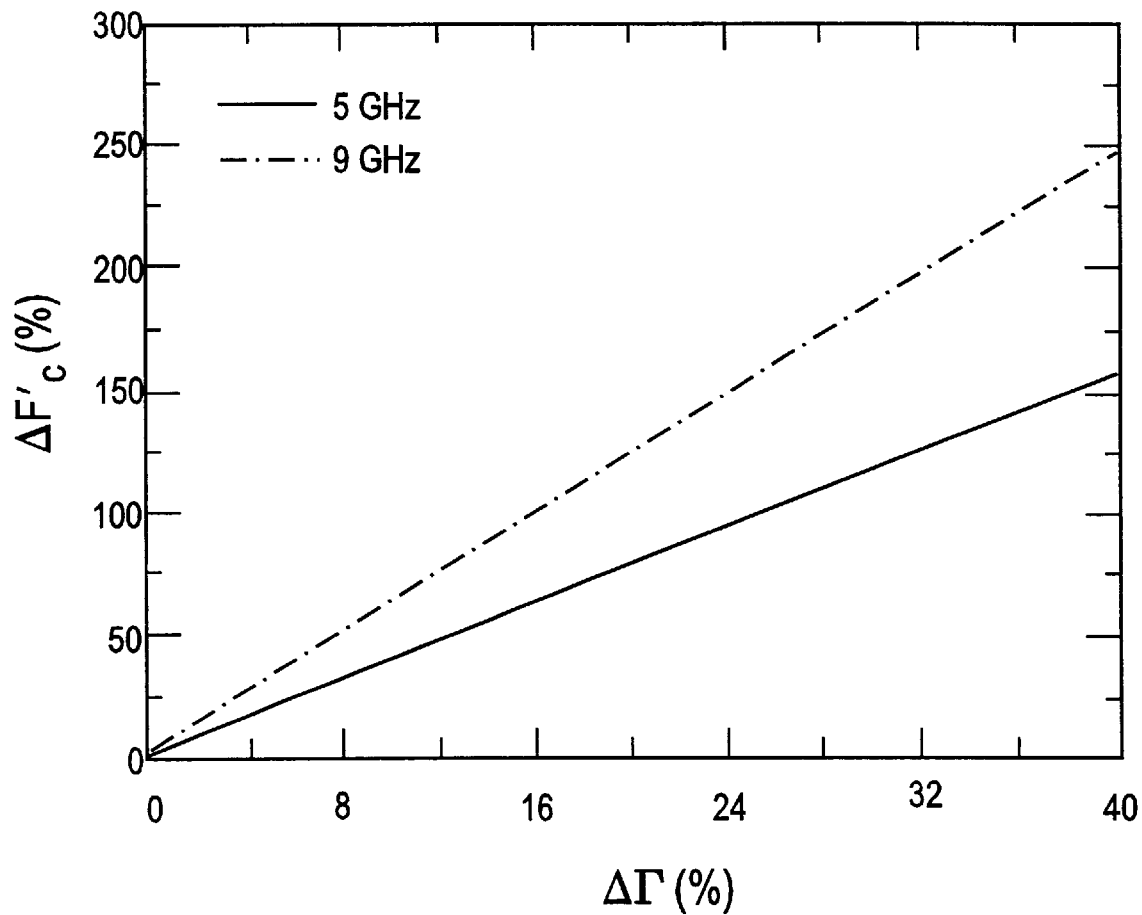
FIG. 7 is a graph illustrating the percentage change (based on a w/c ratio of 0.6) in cement paste compressive strength as a function of the percentage change (based on a w/c ratio of 0.6) in reflection coefficient magnitude for two different frequencies.

With reference to FIG. 7, a relationship is defined between percentage changes in concrete compressive strength for the cement paste samples ($\Delta f_c$) and percentage changes in reflection coefficient magnitudes ($\Gamma\Delta$). Since the reflection coefficient magnitude is measurable, this compressive strength parameter can be directly found once the reflection coefficient magnitude is measured. As seen in FIG. 7, such a determination related to concrete compressive strength may vary as a function of the transmitted microwave frequency. A swept frequency could be utilized to provide an average measured value of the reflection coefficient magnitude.

Referring back to FIG. 1, the automatic determination and display of concrete strength related parameters can be further described. The storage memory 64 may include the steps or algorithm implemented in software for executing one or more logarithmic equations based, for example, on equations (8) and (9). In particular, the crystal detector 52 provides a signal related to the measured reflection coefficient magnitude. That is, the crystal detector output is used with equation (1) to determine $\Gamma$ for the concrete being tested. The determined value of $\Gamma$ is then used by the software to calculate the w/c ratio for the sample using one or both of equations (8) and (9). In the case of more than one microwave frequency being used, the w/c ratio could be determined from a number of microwave frequencies by taking an average or a weighted average of the determined w/c ratios. In the case of a weighted average, greater weight may be given to w/c ratios determined at lower frequencies. Alternatively, a single value of a reflection coefficient magnitude may be obtained, but with this single value possibly being an average or weighted average based on swept frequency measurements. The storage memory 64 may also include software for implementing steps of an algorithm useful in determining concrete compressive strength, such as based on equation (10). That is, for example, after the w/c ratio is determined for the sample, software can be executed using the determined value of the w/c ratio in order to determine the concrete compressive strength.

In a related embodiment, instead of implementing the equations using software, one or more memory tables could be stored in the storage memory 64. These tables could include data that provides a correlation between a measured reflection coefficient magnitude and a concrete strength parameter. One memory table could include a number of reflection coefficient magnitude values. For each value of the reflection coefficient magnitude, a correlating or corresponding w/c ratio value would be provided. Another memory table could correlate values of reflection coefficient magnitudes and values related to concrete compressive strength. It may also be desirable to include software executable by the processing unit 60 that linearly, or otherwise, extrapolates between adjacent data or values of reflection coefficient magnitudes and w/c ratios and/or compressive strength values. Regardless of the embodiment utilized, after the processing unit 60 executes the appropriate software for determining the desired concrete strength related parameters, this value or values is inputted to the display unit 68 for providing an essentially real time display of the desired concrete strength related parameter(s) for the concrete sample under test.

It should also be understood that the algorithm that is utilized for determining a concrete strength related value may or need not be based on a logarithmic function. Instead of a logarithmic equation, the derived relationship for correlating $\Gamma$ and concrete strength may be based on one or more other numerically determined equations, such as a power equation.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiment described hereinabove is further intended to explain the best mode presently known of practicing the invention and to enable others skilled in the art to utilize the invention in such, or other embodiments, and with the various modifications required by their particular application or uses of the invention. It is intended that the appended claims be construed to include alternative embodiments to the extent permitted by the prior art.

What is claimed is:

1. A method for analyzing concrete, comprising:

transmitting a first microwave signal having a first frequency that is directed to concrete being tested having unknown water and cement proportions;

receiving a reflected microwave signal resulting from at least portions of said transmitted microwave signal being reflected by the concrete;

providing a first value related to a reflection coefficient for a concrete sample having known water and cement proportions;

obtaining a second value related to a reflection coefficient based upon at least said reflected microwave signal from the concrete being tested;

determining a difference magnitude related to a difference between said first value and said second value;

having analysis information related to correlating said difference magnitude and one of a plurality of strength related values for the concrete being tested; and determining a strength related value for the concrete being tested using said difference magnitude and said analysis information.

2. A method, as claimed in claim 1, wherein:

said having step includes storing in memory said analysis information that includes equation derived information based on a number of values of at least water/cement ratios.

3. A method, as claimed in claim 1, wherein:

said transmitting step includes transmitting a second microwave signal having a second frequency that is directed to the concrete being tested, said second frequency being different from said first frequency.

4. A method, as claimed in claim 3, wherein:

said obtaining step includes obtaining a third value related to another reflection coefficient using said second microwave signal having said second frequency and said determining step includes using each of said second and third values in determining said one strength related value of the concrete being tested.

5. A method, as claimed in claim 1, wherein:

said having step includes deriving a logarithmic equation based on a number of water/cement ratios and said having step includes providing an algorithm related to solving said logarithmic equation to determine said one strength related value of the concrete being tested.

6. A method, as claimed in claim 1, wherein:

said strength related values include a water/cement ratio and a concrete compressive strength value.

7. A method, as claimed in claim 1, wherein:

said having step includes storing a number of values in storage memory correlating values related to reflection coefficients with said plurality of concrete strength related values.

8. A method, as claimed in claim 1, wherein:

said reflected microwave signal has a magnitude and a phase and said determining step includes determining said one strength related value independently of said phase of said reflected microwave signal.

9. A method, as claimed in claim 1, wherein:

said determining step includes displaying a compressive strength value for the concrete being tested.

10. An apparatus for analyzing concrete, comprising:

first means for transmitting a microwave signal having a first frequency;

second means for receiving a microwave signal reflected from concrete being tested, said received microwave signal having a magnitude and a phase associated therewith and the concrete being tested having water and cement proportions that are unknown;

third means for storing analysis information that correlates values related to reflection coefficient magnitudes and values related to concrete strength; and processing means for determining a first value related to a reflection coefficient magnitude using said transmitted and said received microwave signals, said processing means for determining a concrete strength related value for the concrete being tested using said analysis information and said first value, said concrete strength related value being determined independently of said phase associated with said received microwave signal and said concrete strength related value being determined in the absence of knowing, before said determination, water and cement proportions of the concrete being tested.

11. An apparatus, as claimed in claim 10, wherein:

said analysis information includes at least an equation that is solved in a number of steps using said first value.

12. An apparatus, as claimed in claim 10, wherein:

said first means transmits a microwave signal at a second frequency different from said first frequency and said processing means determines a second value related to a reflection coefficient magnitude using said microwave signal having said second frequency, said second frequency being less than said first frequency.

13. An apparatus, as claimed in claim 10, wherein:

said analysis information includes at least a first equation and said first value is used in said first equation to determine a water/cement ratio for the concrete.

14. An apparatus, as claimed in claim 13, wherein:

said first equation is derived from a number of values related to reflection coefficient magnitudes and a number of correlated water/cement ratio values.

15. An apparatus, as claimed in claim 10, wherein:

said strength related value of the concrete being tested includes a water/cement ratio.

16. An apparatus, as claimed in claim 12, wherein:

said first and second values are averaged with a greater relative weight being given to said second value.

17. An apparatus, as claimed in claim 10, further including:

display means communicating with said processing means for displaying said strength related value of the concrete being tested.

18. An apparatus, as claimed in claim 11, wherein:

said equation includes a logarithmic function.

19. An apparatus, as claimed in claim 10, wherein:

said analysis information includes a number of stored values related to reflection coefficient magnitudes correlated with water/cement ratios.

20. An apparatus, as claimed in claim 10, wherein:

said analysis information includes a number of stored values related to reflection coefficient magnitudes correlated with concrete compressive strength values.

21. An apparatus, as claimed in claim 10, wherein:

said values related to reflection coefficient magnitudes stored by said third means are based on concrete samples having known water and cement proportions.

22. An apparatus, as claimed in claim 10, wherein:

said processing means determines a difference between said first value and a value related to a reflection coefficient magnitude for a concrete sample having known water and cement proportions.

23. An apparatus, as claimed in claim 10, wherein:

said first frequency is greater than 3 GHz.

* * * * *